US009362047B2

(12) United States Patent
Krumme

(10) Patent No.: US 9,362,047 B2
(45) Date of Patent: Jun. 7, 2016

(54) CONTACTLESS ROTARY JOINT

(71) Applicant: Nils Krumme, Feldafing (DE)

(72) Inventor: Nils Krumme, Feldafing (DE)

(73) Assignee: SCHLEIFRING UND APPARATEBAU GMBH, Fürstenfeldbruck (DE)

( * ) Notice: Subject to any disclaimer, the term of this patent is extended or adjusted under 35 U.S.C. 154(b) by 628 days.

(21) Appl. No.: 13/851,306

(22) Filed: Mar. 27, 2013

(65) Prior Publication Data

US 2013/0214614 A1    Aug. 22, 2013

Related U.S. Application Data

(63) Continuation of application No. PCT/EP2011/062529, filed on Jul. 21, 2011.

(51) Int. Cl.
| H01F 38/14 | (2006.01) |
| A61B 6/00 | (2006.01) |
| H01F 38/18 | (2006.01) |
| H04B 5/00 | (2006.01) |
| H02J 5/00 | (2016.01) |
| H02J 17/00 | (2006.01) |

(52) U.S. Cl.
CPC .............. *H01F 38/14* (2013.01); *A61B 6/4488* (2013.01); *A61B 6/56* (2013.01); *H01F 38/18* (2013.01); *H02J 5/005* (2013.01); *H02J 17/00* (2013.01); *H04B 5/0012* (2013.01); *H04B 5/0031* (2013.01); *H04B 5/0037* (2013.01)

(58) Field of Classification Search
CPC ........... H01F 38/14; H01F 38/18; A61B 6/56; A61B 6/4488; H04B 5/0012; H04B 5/0031
USPC ........................................................ 307/104
See application file for complete search history.

(56) References Cited

U.S. PATENT DOCUMENTS

| 5,577,026 | A | 11/1996 | Gordon et al. | |
| 5,814,900 | A | 9/1998 | Esser et al. | |
| 6,472,791 | B1 | 10/2002 | Rehder et al. | |
| 2005/0135551 | A1 | 6/2005 | Katcha et al. | |
| 2007/0035883 | A1* | 2/2007 | Katcha ..................... | A61B 6/56 360/281.8 |
| 2007/0188284 | A1* | 8/2007 | Dobbs ...................... | A61B 6/56 336/120 |
| 2008/0049904 | A1* | 2/2008 | Beyerlein ................. | A61B 6/56 378/197 |
| 2009/0185658 | A1* | 7/2009 | Katcha ................... | G08C 17/04 378/15 |

FOREIGN PATENT DOCUMENTS

| DE | 84 29 531 U1 | 4/1986 |
| WO | 2009/033573 A1 | 3/2009 |

OTHER PUBLICATIONS

International Search Report as mailed on Nov. 4, 2011 for International Application No. PCT/EP2011/062529.
European Patent Office, Extended Search Report, Application No. 15169494.0, Oct. 22, 2015.

* cited by examiner

*Primary Examiner* — Scott Bauer
(74) *Attorney, Agent, or Firm* — Yakov Sidorin; Quarles & Brady, LLP

(57) ABSTRACT

A contactless rotary joint has a stationary and a rotating part. Furthermore at least one of the parts has a rotary joint body made of a plastic material and holding a capacitive data link and a rotating transformer. The rotating transformer has a magnetic core for transmission of electrical power. To prevent interference of the capacitive data link by electrical and/or magnetic fields from the rotating transformer a shield is provided.

19 Claims, 7 Drawing Sheets

CONTACTLESS ROTARY JOINT

CROSS-REFERENCE TO RELATED APPLICATIONS

This application is a continuation of the International Patent Application No. PCT/EP2011/062529 filed on Jul. 21, 2011, which designates the United States and claims priority from the German Patent Application No. 10 2010 041 573 filed on Sep. 28, 2010. The present application claims priority from and incorporates by reference each of the above-mentioned applications.

BACKGROUND

The invention relates to contactless rotary joints and, in particular, the contactless rotary joints adapted for use in CT scanners. In general, these contactless rotary joints have at least one inductive power coupler configured to transfer power at high levels and a high-speed data link for broadband transmission of data.

A contactless rotary joint with an inductive power coupler and a bidirectional high-speed data link is disclosed in U.S. Pat. No. 7,717,619 B2. Such a rotary joint is able to transfer power of more than hundred kilowatts and data in the 10 Gbit/s range. Due to the high level of power coupled by the inductive power coupler, which is based on a rotating transformer, there may be interference to the data link. Such interference may lead to data loss or even to a complete failure of the data link. To reduce the interference, preferably the magnetic cores of the rotating transformer are E-shaped and have differential windings. As power-level requirements and data rates are increasing further, the risk of interference increases. When the power level in the rotating transformer and, therefore, the stray fields increase, the bandwidth and therefore the sensitivity of the data link also increases.

SUMMARY

Embodiments of the present invention are directed to improve contactless rotary joints by further minimizing the risk of interference even when the power level in the rotating transformer and the bandwidth of the data link increases. A further object of the invention is to reduce coupling between a rotating transformer and a contactless data link. Another object of the invention is to provide measures that may be implemented on a non-metal rotary joint body.

Rotating transformers produce stray electric and magnetic fields. One goals targeted when designing a rotating transformer is to keep the magnetic field flux substantially confined within pre-determined areas. For this purpose often soft magnetic cores (such as, for example, specific ferrite or iron cores) are used. Generally, a rotating transformer has a gap between the rotating parts that facilitates the rotation. In the CT scanners, for example, the gap is comparatively broad as the rotating part of the gantry is comparatively heavy. In some cases, the gantry may even be tilted and therefore requires additional space for the mechanical movement between the rotating and stationary part, which may lead to a gap in the range of about 1 mm. This gap and limited magnetic conductivity of the magnetic cores causes magnetic stray field.

In addition to the magnetic fields, a rotating transformer also generates strong electric fields. The windings of the rotating transformer carry significant voltages (which may be in an order of magnitude of 500 Volts) and currents. Furthermore, the switching semiconductors supplying the AC voltage to the transformer windings cause high-frequency peaks. Due to the high power and the resulting high magnetic flux, the magnetic core has a comparatively large cross section forming a comparatively high capacitance with respect to any other component in its proximity. Therefore, the electric fields generated by the rotating transformer can interfere with operation of other components. One means of reducing the operational interference is keeping the distance between the interfering parts.

In general electric and magnetic fields can affect data transmission of a capacitive data link. The capacitive data link may generate significant common mode voltage in the data link's transmission line. Other electronic and mechanical parts may also be affected by electric and magnetic fields formed by the rotating transformer. For example, the bearing between the rotating and the stationary part of the gantry may corrode due to currents flowing through the bearing between rotating and stationary parts.

The idea of the present invention is in diversion of electric and magnetic fields and the voltages and currents generated by the rotating transformer.

In general, a contactless rotary joint has a rotary joint body which carries the components necessary for transferring electrical signals or power. The rotary joint body may be made of metal which gives a high mechanical stability and provides for some shielding between the individual components. The drawback manifests in close electrical coupling between the components attached thereto, which again increases the operational interference. Furthermore, metal structures are generally radiating high-frequency signals as they are transmitted by the capacitive data link transmission lines.

The embodiments provide solutions for reducing interference in non-metal or plastic materials rotary joint bodies. In general, rotary joint systems include the first rotary joint body and second rotary joint body mounted rotatable in close proximity to each other. The first and second rotary joint bodies are generally very similar and almost symmetrical to each other. In most cases there is a capacitive data link including a transmission line and a transmitter and an inductive transformer including a transformer magnetic core with windings attached to a rotary joint body.

In a preferred embodiment at least one shielding is provided. The shielding preferably reduces interference from the rotating transformer. Such a shielding is preferably a conducting backplane mounted to a side of the rotary joint body opposing the rotating transformer magnetic core.

In a further embodiment there is an inner shield within the rotary joint body located between the rotating transformer magnetic core and the capacitive data link transmission line. In one implementation, this shield may be molded into the rotary joint body.

A further preferred embodiment relates to a core shield which at least partially encloses the rotating transformer magnetic core.

In another embodiment, at least one shield has a higher thermal conductivity than the rotary joint body. Therefore it facilitates the dissipation of heat from the rotating transformer. Preferably at least one shield is thermally connected to the rotating transformer core. For further improving heat dissipation to be environment at least one fin is provided, which is thermally connected to the shield.

In another embodiment there is a magnetic core shield surrounding the backside of the rotating transformer magnetic core.

In a further embodiment the backplane includes a material with soft magnetic properties for an improved shielding of magnetic fields.

In a further embodiment the transmission line may have multiple segments for transmission of data.

In a further embodiment at least one winding may have multiple segments.

In a further embodiment, a shielded temperature sensor may be provided. This temperature sensor has a sensor shield which is electrically connected to the shield and preferably to the backplane. Furthermore the sensor is thermally coupled to at least one of magnetic core or winding.

In a further embodiment a metal tape is mounted to the rotary joint body. The metal tape has openings, preferably slits or holes. These openings may be optically or magnetically detected for identifying the position of the tape and therefore the position of the rotary joint body.

In general the concepts shown herein may also be used for other types of contactless transformers like linear movable couplers.

BRIEF DESCRIPTION OF THE DRAWINGS

In the following, embodiments of the invention are described in reference to examples, drawings, and without limitation of the general inventive concept.

Figure 1:
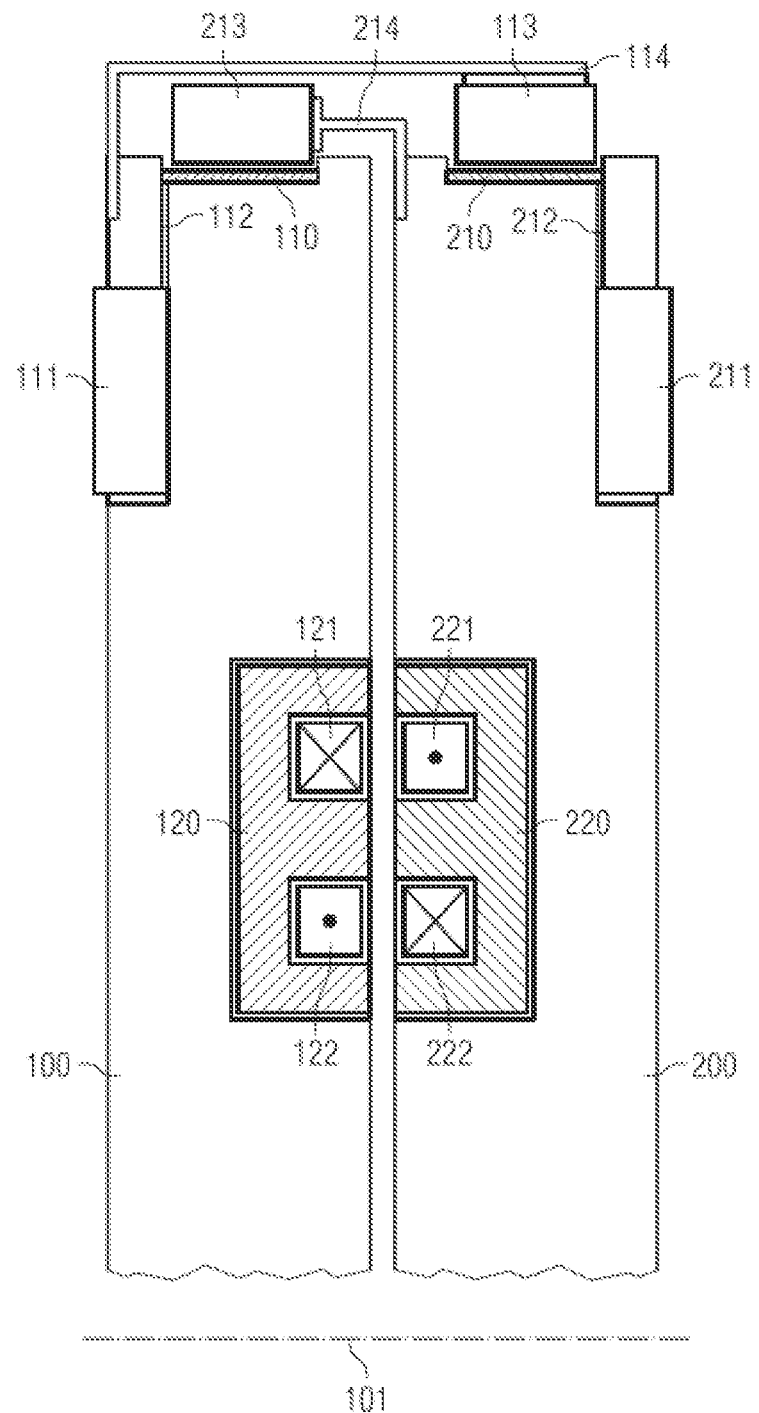
FIG. 1 shows a basic contactless rotary joint.

While embodiments of the invention can be modified and presented in alternative forms, specific embodiments thereof are shown by way of example in the drawings and are described below in detail. The provided drawings and detailed description are not intended to limit the invention to the particular form disclosed, but on the contrary, the intention is to cover all modifications, equivalents and alternatives falling within the spirit and scope of the present invention as defined by the appended claims.

DETAILED DESCRIPTION

An embodiment of FIG. 1 shows a basic contactless rotary joint. The joint includes a primary part and a secondary part which are rotatable against each other around the rotation axis 101. The primary part and the secondary part are very similar. In the embodiments shown herein the primary part has a rotary joint body 100 that carries the other rotary joint components. Preferably the rotary joint body is shaped as a disk. It may also be drum shaped. In most cases, the rotary joint body includes a free inner bore. This is specifically required in computer tomography (CT) scanners for accommodating the patient. One of the components attached to or incorporated into the body is a contactless data link, which is shown as a capacitive data link transmission line 110 in this embodiment. The contactless data link is connected to a data transmitter 111 with connecting line 112. The data link transmission line 110 is almost encircling the rotary joint body 100, thus allowing data transmission independent of rotation angle. The data link receiver 213 is located at a predetermined position and not encircling the body. It is mounted rotatable in close proximity of the transmission line to pick up signals emitted by the transmission line. The data link receiver 213 is attached to the secondary side by means of a second bracket 214. Therefore, the data link receiver 213 is movable against data link transmission line 110 during rotation. This contactless data link may communicate data from the primary part to the secondary part. For transmission of power, a rotating transformer is provided. It includes a magnetic core 120. In this embodiment it is an E-shaped core having a forward winding 121 and a backward winding 122. Preferably, the windings are made of litz wire. The magnetic core may include a plurality of individual core segments.

Opposed to the primary part is a secondary part which has a secondary rotary joint body 200. It further includes a second capacitive data link with a transmission line 210 fed via a second connecting line 212 by a second data transmitter 211. The second capacitive data link is enabled to transfer data from the secondary part to the primary part. It also has a data receiver 113, which is mounted by the bracket 114 to the rotary joint body 100. In the embodiment of FIG. 1, a capacitive data link is shown for each direction. However, there may be only one data link for only one direction. In general, in CT scanners at least one data link from the rotating part to the stationary part is required. Furthermore a second rotating transformer is provided having a second rotating transformer magnetic core 220 and a second forward winding 221 as well as a second backward winding 222.

The rotating transformer cores of the primary side 120 and the secondary side 220 are mounted in close proximity to one another to allow for coupling of their magnetic fields.

It can be seen that the primary side (having rotary joint body 100) and secondary side (having rotary joint body 200) are substantially symmetric and identical. Therefore, in a further discussion references directed only to the rotary joint body 100 and the parts attached thereto are considered to be equally applicable to the rotary joint body 200 and its corresponding parts. The second part may be made symmetrical to the first one.

Rotary joint body 110 is preferably made of a plastic material providing isolation to the components mounted thereon or therein. This rotary joint body may also be made of metal providing electric shielding and good heat dissipation. The main disadvantage of a metal rotary joint body is the comparatively high costs associate with its fabrication and exploitation. Furthermore, a metal rotary joint body tends to radiate RF signals from the transmission line 110 as it is connected to the ground of this transmission line. Electrical isolation between the transmission line and a metal rotary joint body 110 is substantially complex as it is required that such isolation have a comparatively low capacitance.

Figure 2:
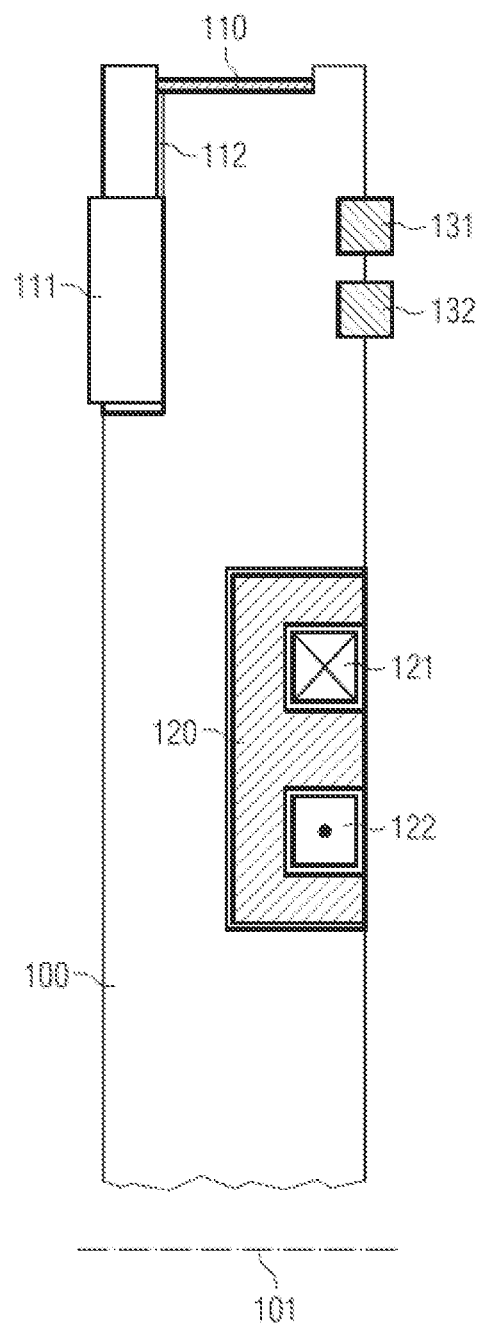
FIG. 2 shows an embodiment with a slip ring track.

In FIG. 2 another embodiment is shown. Here, an additional first slipring track 131 and a second slipring track 132 are provided that are adapted to transfer auxiliary signals or standby power. They may further be used for grounding. In this case, the slipring tracks may be connected to at least one of the metal planes, structures or shield shown herein. Here, the corresponding secondary side rotary joint body would not have further slipring tracks but slipring brushes to interface with these tracks. There may be one or any other number of slipring tracks. Furthermore, there may be slipring tracks on the secondary side and corresponding brushes on the primary side.

Figure 3:
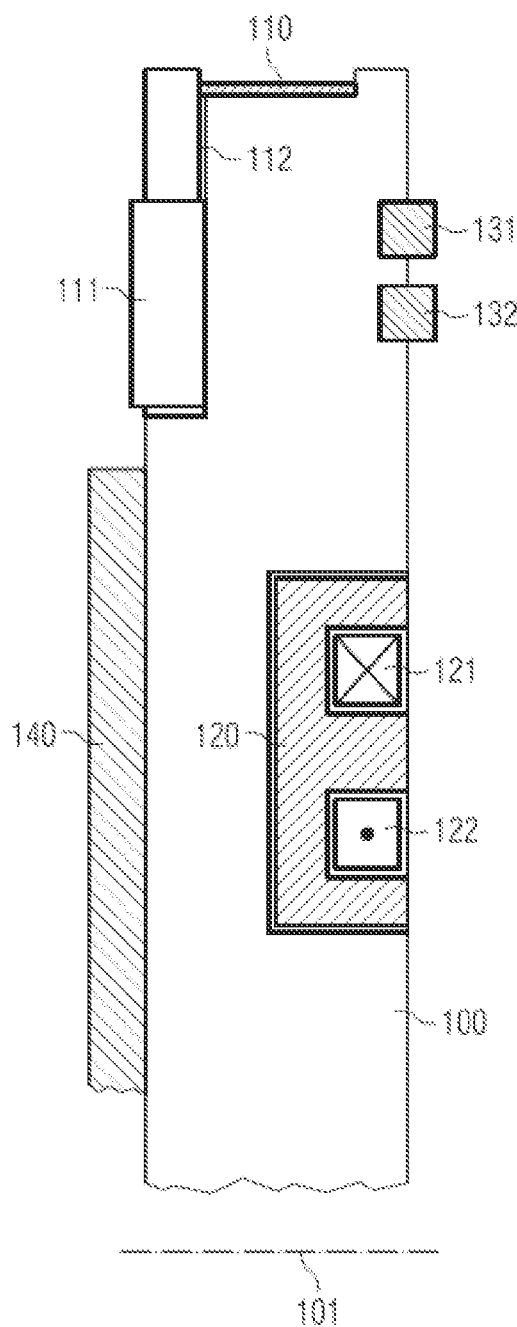
FIG. 3 shows an embodiment with a conducting backplane.

In FIG. 3, a further embodiment having a conducting backplane 140 is shown, which is preferably a metal plate or foil but may include any other electrically conducting material adapted to act as a shield. The metal structure acts as a reference plane for the field of the windings contained within magnetic core 120. It is configured as a shield for the electric stray fields and parts of the magnetic stray fields of the magnetic core. When the conducting backplane 140 is electrically connected to a magnetic core 120, there is a current between them.

Figure 4:
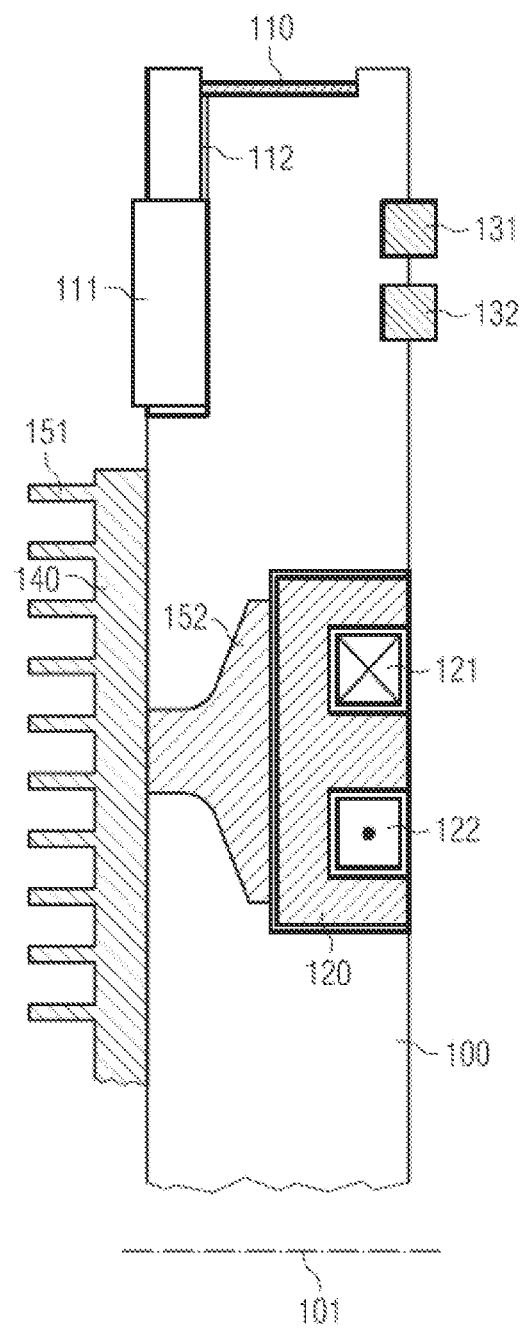
FIG. 4 shows an embodiment adapted for improved heat dissipation.

In FIG. 4 illustrates another embodiment structured for improved heat dissipation. The conducting backplane may also improve heat dissipation of the rotating transformer. For this purpose, the conducting backplane has higher heat conductivity than that of the rotary joint body. It may further include at least one fin 151 to improve heat transfer and heat dissipation to the environment. It is also preferred for the backplane to have at least one heat conductor 152 to the rotating transformer for improving heat transfer. There may also be a heat conducting material between the inductive transformer and the backplane. Furthermore, it is preferred if this heat conducting material includes an isolator. It is further preferred, if the distance between the rotating transformer magnetic core 120 and the backplane 140 is minimized (for example, reduced to below 5 mm) to improve heat transfer. Furthermore, there may be guiding structures within the rotary joint body or the backplane to generate an additional airflow to the rotating transformer magnetic core 120.

Figure 5:
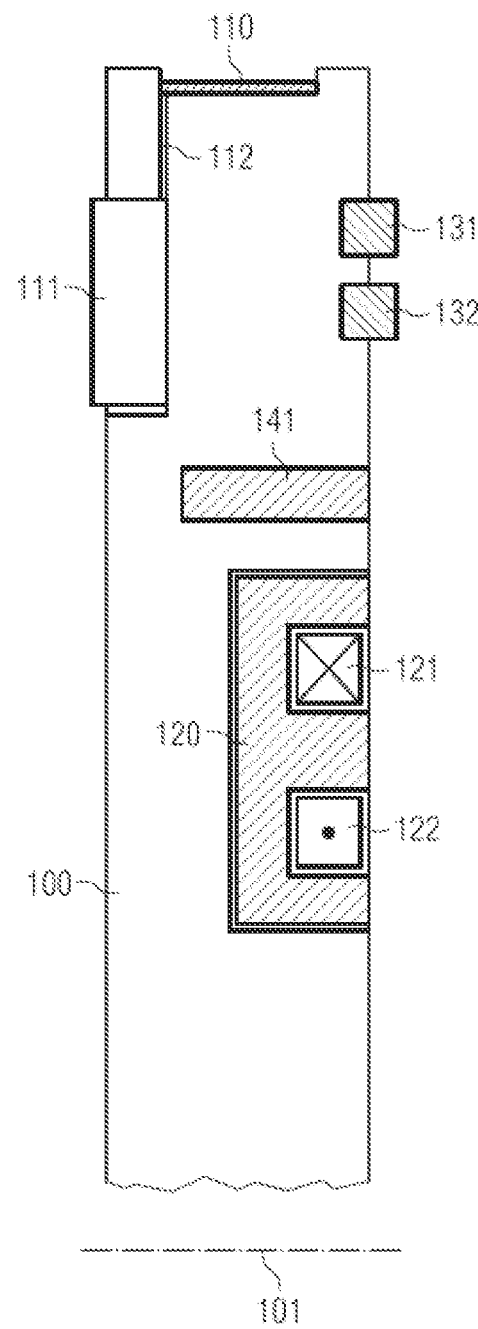
FIG. 5 shows an embodiment with an inner shield.

In FIG. 5, an embodiment having an inner shield 141 is shown. This inner shield 141 prevents interfering of fields generated from the rotating transformer with the capacitive data link. Preferably the inner shield 141 is structured as a closed ring. It furthermore is connected to the system ground. It preferably includes a soft magnetic material to improve shielding. It may include a metal sheet, a mesh or a foil. It may preferably be cast or molded into the rotary joint body 100.

Figure 6:
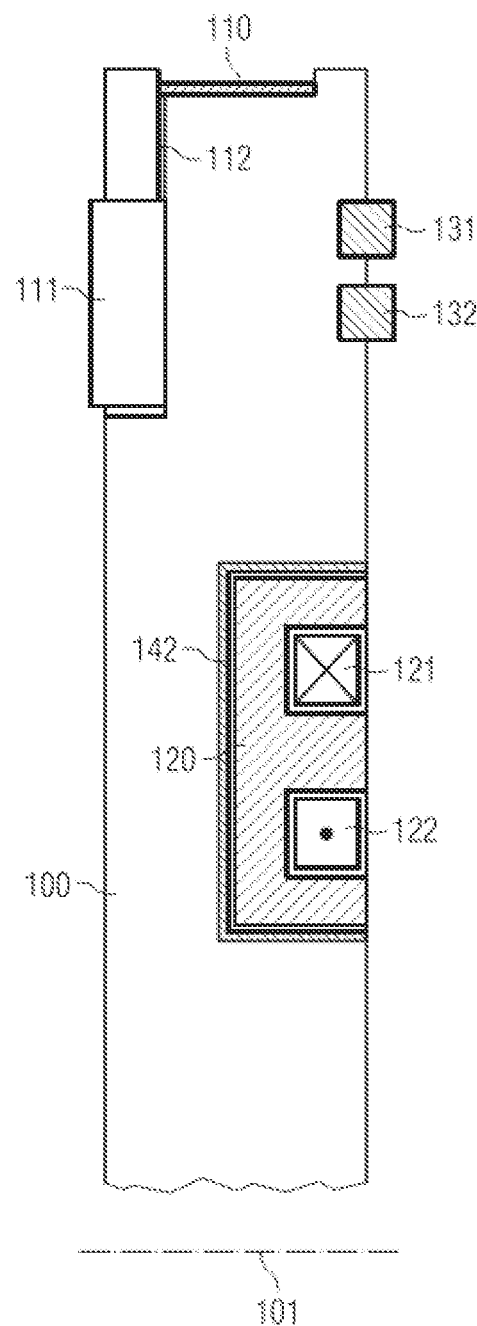
FIG. 6 shows an embodiment with the magnetic core shield.

FIG. 6 shows an embodiment with the magnetic core shield 142. Here the core shield preferably surrounds magnetic core 120. It completely encloses the free sides of the magnetic core to offers the optimized shielding.

Figure 7:
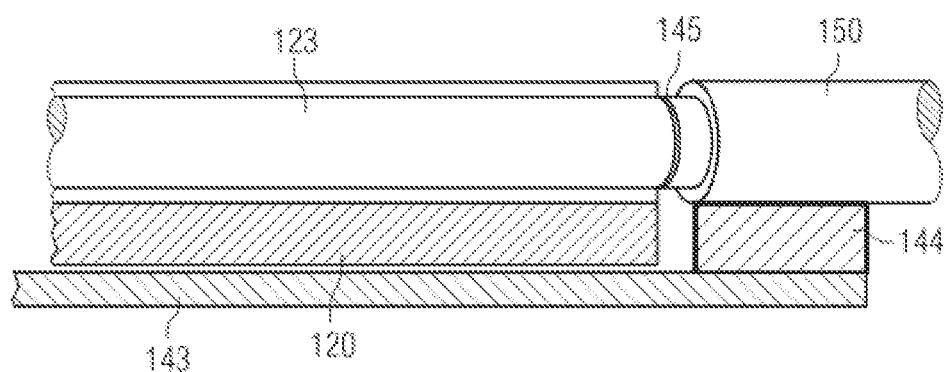
FIG. 7 shows an electrical shield connection.

In FIG. 7, an electric shield connection is shown. The wire of a winding 123 (which may be any one of forward winding 121 or backward winding 122) is within rotating transformer magnetic core 120. It is connected to a shielded cable 150 by cable connection 145. The shield of the shielded cable 150 is connected to shield 143 which may be any of the shields disclosed herein by a low impedance and/or low resistance connection 144. The connections may be crimping, soldering or welding connections.

It will be appreciated to those skilled in the art having the benefit of this disclosure that this invention is believed to provide contactless rotary joints. Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

LIST OF REFERENCE NUMERALS

100 rotary joint body
101 rotational axis
110 capacitive data link
111 data transmitter
112 connecting line
113 data receiver
114 receiver bracket
120 rotating transformer magnetic core
121 forward winding
122 backward winding
123 winding
131 first slipring track
132 second slipring track
140 conducting backplane shield
141 inner shield
142 core shield
143 shield
144 shield connection
145 cable connection
150 shielded cable
151 fins
152 heat conductor
200 second rotary joint body
210 second capacitive data link
211 second data transmitter
212 second connecting line
113 second data receiver
114 second receiver bracket
220 second rotating transformer magnetic core
221 second forward winding
222 second backward winding

The invention claimed is:

1. A contactless rotary joint having stationary and rotating parts, at least one of the stationary and rotating parts including:
    a rotary joint body of a plastic material and shaped as a disk,
    a capacitive data link juxtaposed with the rotary joint body and having a data transmission line configured to transmit data, and
    a rotating transformer with a magnetic core configured to transmit electrical power, said core having at least one winding,
    wherein at least one shield is configured to shield at least one of electrical and magnetic fields generated by the rotating transformer such as to reduce interference with the capacitive data link, a thermal conductivity of the at least one shield being higher than that of the rotary joint body to improve dissipation of heat from the rotating transformer,
    wherein the rotating transformer magnetic core is held at one side of the disc, while a conducting backplane is mounted to an opposite side of the disc.

2. The contactless rotary joint according to claim 1, wherein the at least one shield is thermally connected to the rotating transformer magnetic core.

3. The contactless rotary joint according to claim 1, wherein the at least one shield has at least one fin dimensioned to increase heat dissipation to the environment.

4. The contactless rotary joint according to claim 1, wherein the at least one shield includes an inner shield molded into the rotary joint body.

5. The contactless rotary joint according to claim 1, wherein the at least one shield includes a core shield configured to at least partially enclose the rotating transformer magnetic core.

6. The contactless rotary joint according to claim 1, wherein the rotating transformer has at least one winding that is connected to an inverter by a shielded cable, wherein a shield of the shielded cable is connected to the at least one shield and an inner conductor is connected to the at least one winding.

7. The contactless rotary joint according to claim 1, wherein the conducting backplane includes a material having soft magnetic properties.

8. The contactless rotary joint according to claim 1, wherein the data transmission line has multiple segments for transmission of data.

9. The contactless rotary joint according to claim 1, wherein the at least one winding has multiple segments.

10. The contactless rotary joint according to claim 1, further including a shielded temperature sensor thermally coupled to at least one of the magnetic core and the at least one winding and wherein a shield of the shielded temperature sensor is electrically connected to the conducting backplane.

11. The contactless rotary joint according to claim 1, further including a metal tape mounted to the rotary joint body, the metal tape having openings configured to enable at least one of optical and magnetic reading of a position of the tape to determine a position of the rotary joint body.

12. A contactless rotary joint having stationary and rotating parts, at least one of the stationary and rotating parts including:
   a rotary joint body of a plastic material,
   a capacitive data link juxtaposed with the rotary joint body and having a data transmission line configured to transmit data, and
   a rotating transformer with a magnetic core configured to transmit electrical power, the core having at least one winding,
   wherein at least one shield is configured to shield at least one of electrical and magnetic fields generated by a rotating transformer such as to reduce interference with the capacitive data link, a thermal conductivity of the at least one shield being higher than that of the rotary joint body to improve dissipation of heat from the rotating transformer, and
   further including a metal tape mounted to the rotary joint body, the metal tape having openings configured to enable at least one of optical and magnetic reading of a position of the tape to determine a position of the rotary joint body.

13. The contactless rotary joint according to claim 12, wherein the at least one shield is thermally connected to the magnetic core.

14. The contactless rotary joint according to claim 12, wherein the at least one shield has at least one fin dimensioned to increase heat dissipation to the environment.

15. The contactless rotary joint according to claim 12, wherein the rotary joint body has a disc shape, and the rotating transformer magnetic core is held at one side of the disc, while a conducting backplane is mounted to an opposing side of the disc.

16. The contactless rotary joint according to claim 15, wherein the conducting backplane includes a material having soft magnetic properties.

17. The contactless rotary joint according to claim 12, wherein the at least one shield includes an inner shield molded into the rotary joint body.

18. The contactless rotary joint according to claim 12, wherein the at least one shield includes a core shield configured to at least partially enclose the rotating transformer magnetic core.

19. The contactless rotary joint according to claim 12, wherein the data transmission line has multiple segments for transmission of data.

* * * * *